US009682025B2

(12) United States Patent
Mahe et al.

(10) Patent No.: US 9,682,025 B2
(45) Date of Patent: Jun. 20, 2017

(54) COMBINATION OF ACTIVE AGENTS FOR ORAL ADMINISTRATION FOR IMPROVING THE QUALITY OF NAILS

(71) Applicant: NUTRICOS TECHNOLOGIES, Clichy (FR)

(72) Inventors: Yann Mahe, Sainte Genevieve des Bois (FR); Carole Bru, Courbevoie (FR); Nathalie Piccardi, Arceau (FR); Audrey Gueniche, Rueil Malmaison (FR)

(73) Assignee: NUTRICOS TECHNOLOGIES, Clichy (FR)

( * ) Notice: Subject to any disclaimer, the term of this patent is extended or adjusted under 35 U.S.C. 154(b) by 0 days.

(21) Appl. No.: 14/890,071

(22) PCT Filed: May 6, 2014

(86) PCT No.: PCT/IB2014/061247
§ 371 (c)(1),
(2) Date: Nov. 9, 2015

(87) PCT Pub. No.: WO2014/181259
PCT Pub. Date: Nov. 13, 2014

(65) Prior Publication Data
US 2016/0095803 A1 Apr. 7, 2016

(30) Foreign Application Priority Data
May 7, 2013 (FR) ...................... 13 54190

(51) Int. Cl.
| A61K 8/36 | (2006.01) |
| A61K 8/27 | (2006.01) |
| A61K 8/31 | (2006.01) |
| A61K 8/44 | (2006.01) |
| A61K 8/46 | (2006.01) |
| A61Q 3/00 | (2006.01) |
| A61K 8/92 | (2006.01) |
| A61K 8/97 | (2017.01) |
| A61K 8/43 | (2006.01) |
| A61K 8/58 | (2006.01) |
| A61K 8/67 | (2006.01) |
| A61Q 3/02 | (2006.01) |
| A23L 33/12 | (2016.01) |

(52) U.S. Cl.
CPC .............. *A61K 8/361* (2013.01); *A23L 33/12* (2016.08); *A61K 8/27* (2013.01); *A61K 8/31* (2013.01); *A61K 8/43* (2013.01); *A61K 8/44* (2013.01); *A61K 8/447* (2013.01); *A61K 8/466* (2013.01); *A61K 8/58* (2013.01); *A61K 8/67* (2013.01); *A61K 8/678* (2013.01); *A61K 8/922* (2013.01); *A61K 8/97* (2013.01); *A61Q 3/00* (2013.01); *A61Q 3/02* (2013.01); *A23V 2002/00* (2013.01); *A61K 2800/92* (2013.01)

(58) Field of Classification Search
None
See application file for complete search history.

(56) References Cited

U.S. PATENT DOCUMENTS

| 3,395,236 | A | 7/1968 | White |
| 4,097,604 | A | 6/1978 | Thiele |
| 6,139,852 | A | 10/2000 | Takeoka et al. |
| 6,270,811 | B1 | 8/2001 | Fregonese |
| 6,331,569 | B1 * | 12/2001 | Kisters ................... A61K 8/447 514/561 |
| 6,362,221 | B1 | 3/2002 | Clark et al. |
| 6,365,175 | B1 | 4/2002 | Alaluf et al. |
| 2002/0034485 | A1 | 3/2002 | Noser et al. |
| 2003/0054015 | A1 | 3/2003 | Haze et al. |
| 2005/0175565 | A1 | 8/2005 | Duranton et al. |
| 2006/0068046 | A1 | 3/2006 | Arita et al. |
| 2006/0269508 | A1 | 11/2006 | Trejo |
| 2008/0248130 | A1 * | 10/2008 | Rath .................... A61K 31/198 424/638 |
| 2008/0319071 | A1 | 12/2008 | Raederstorff et al. |
| 2009/0169652 | A1 | 7/2009 | Osborne |
| 2010/0022648 | A1 * | 1/2010 | Gueniche ............... A61K 8/361 514/560 |
| 2010/0291012 | A1 | 11/2010 | Guy et al. |
| 2011/0008308 | A1 * | 1/2011 | Taylor .................. A61K 8/0216 424/94.1 |
| 2012/0308586 | A1 | 12/2012 | Garcia Villarrubia et al. |
| 2013/0302297 | A1 | 11/2013 | Gueniche et al. |

FOREIGN PATENT DOCUMENTS

| BE | 1019927 A3 | 2/2013 |
| CN | 101265177 A | 9/2008 |
| CN | 101453914 A | 6/2009 |

(Continued)

OTHER PUBLICATIONS

Roland et al. (EP0679383 A1).*
U.S. Appl. No. 14/889,984, filed Nov. 9, 2015 in the name of Mahe et al.
U.S. Appl. No. 14/890,064, filed Nov. 9, 2015 in the name of Mahe et al.
U.S. Appl. No. 14/889,895, filed Nov. 9, 2015 in the name of Mahe et al.
U.S. Appl. No. 14/890,069, filed Nov. 9, 2015 in the name of Mahe et al.
Oct. 21, 2014 International Search Report issued in International Patent Application No. PCT/IB2014/061247.

(Continued)

*Primary Examiner* — Robert A Wax
*Assistant Examiner* — Quanglong Truong
(74) *Attorney, Agent, or Firm* — Oliff PLC

(57) ABSTRACT

The invention relates to the cosmetic use, by oral administration, of a combination of active agents including at least petroselinic acid and at least one active agent selected from among taurine, arginine, cysteine, zinc, a salt thereof, and lycopene, for improving the quality of nails, specifically the microvascularization of the nails, in particular in pre-hypertensive individuals.

18 Claims, No Drawings

(56) References Cited

FOREIGN PATENT DOCUMENTS

| | | | |
|---|---|---|---|
| CN | 102 293 312 A | 12/2011 | |
| DE | 100 35 735 A1 | 9/2001 | |
| DE | 103 25 159 A1 | 12/2003 | |
| DE | 10 2005 057292 A1 | 6/2007 | |
| EP | 0 116 439 A2 | 8/1984 | |
| EP | 0 355 842 A2 | 2/1990 | |
| EP | 0 679 383 A1 | 11/1995 | |
| EP | 0 709 084 A2 | 5/1996 | |
| EP | 0 888 773 A1 | 1/1999 | |
| EP | 1 013 178 A1 | 6/2000 | |
| EP | 1 932 509 A1 | 6/2008 | |
| FR | 1 603 765 A | 5/1971 | |
| FR | 2 569 347 A1 | 2/1986 | |
| FR | 2 756 181 A1 | 5/1998 | |
| FR | 2 939 040 A1 | 6/2010 | |
| FR | 2 952 304 A1 | 5/2011 | |
| GB | 2 458 466 A | 9/2009 | |
| JP | 59172411 A | 9/1984 | |
| JP | H01-275514 A | 11/1989 | |
| JP | 2005-126405 A | 5/2005 | |
| WO | 99/40955 A2 | 8/1999 | |
| WO | WO 9940955 A2 * | 8/1999 | ........... A61F 13/105 |
| WO | 01/08651 A1 | 2/2001 | |
| WO | 02/07700 A2 | 1/2002 | |
| WO | 03/020249 A1 | 3/2003 | |
| WO | 03/075941 A1 | 9/2003 | |
| WO | 2004/000293 A2 | 12/2003 | |
| WO | 2007/122382 A2 | 11/2007 | |
| WO | 2008/071897 A2 | 6/2008 | |
| WO | 2010/080915 A1 | 7/2010 | |
| WO | 2012/059880 A1 | 5/2012 | |
| WO | 2013/068960 A2 | 5/2013 | |

OTHER PUBLICATIONS

Mintel: "Skin, Hair and Nails Food Supplement," GNPD, Nov. 1, 2011, XP002678758, "Product Description," , "Ingredients.".
Oct. 21, 2014 Written Opinion issued in International Patent Application No. PCT/IB2014/061247.
Jul. 8, 2014 International Search Report issued in International Patent Application No. PCT/IB2014/061235.
Jul. 8, 2014 Written Opinion issued in International Patent Application No. PCT/IB2014/061235.
Lacasa, Daniéle et al. "Macrophage-Secreted Factors Impair Human Adipogenesis: Involvement of Proinflammatory State in Preadipocytes." 148(2), pp. 868-877, 2007.
Keophiphat, Mayoura et al. "Macrophage-Secreted Factors Promote a Profibrotic Phenotype in Human Preadipocytes." 23(1), pp. 11-24, 2009.
Salminen, S. et al. "Probiotics: How Should They Be Defined?" Trends in Food Science and Technology, 10, pp. 107-10, 1999.
Gibson R., Glenn and Roberfroid B., Marcel, "Dietary Modulation of the Human Colonic Microbiota: Introducing the Concept of Prebiotics." The Journal of Nutrition, 125, pp. 1401-1412, 1995.
Avato, Pinarosa et al. "The Genus Thapsia as a Source of Petroselinic Acid." 36(8), pp. 845-50, 2001.
Jul. 8, 2014 International Search Report issued in International Patent Application No. PCT/IB2014/061264.
Jul. 8, 2014 Written Opinion issued in International Patent Application No. PCT/IB2014/061264.
Oct. 21, 2014 International Search Report issued in International Patent Application No. PCT/IB2014/061245.
Oct. 21, 2014 Written Opinion issued in International Patent Application No. PCT/IB2014/061245.
Destaillats, Frédéric et al. "Identification of 6-Monosaturated Fatty Acids in Human Hair and Nail Samples by Gas-Chromatography-Mass-Spectrometry Using Ionic-Liquid Coated Capillary Column." Journal of Chromatography A, Elsevier Science Publishers B.V, NL, 1218(52), pp. 9384-9389, 2011.

Singh, Vivek et al. "Availability of Essential Trace Elements in Indian Cereals, Vegetables and Spices Using INAA and the Contribution of Spices to Daily Dietary Intake." Food Chemistry, Elsevier LTD, NL, 94(1), pp. 81-89, 2006.
Oct. 21, 2014 International Search Report issued in International Patent Application No. PCT/IB2014/061246.
Oct. 21, 2014 Written Opinion issued in International Patent Application No. PCT/IB2014/061246.
May 11, 2016 Office Action issued in U.S. Appl. No. 14/890,064.
Placek et al., "A Review on Petroselinic Acid and its Derivatives," Journal of the American Oil Chemists' Society, Aug. 1963, vol. 40, No. 8, pp. 319-329.
Xu et al., "The Potential Health Benefits of Taurine in Cardiovascular Disease," Exp Clin Cardiol, 2008, vol. 13, No. 2; pp. 57-65.
Tsuboyama-Kasaoka et al., "Taurine (2-Aminoethanesulfonic Acid) Deficiency Creates a Vicious Circle Promoting Obesity," Endocrinology, 2006, vol. 147,No. 7, pp. 3276-3284.
Jun. 16, 2016 Office Action issued in U.S. Appl. No. 14/889,984.
Jan. 22, 2016 Office Action issued in U.S. Appl. No. 14/357,335.
Jun. 2, 2016 Office Action issued in U.S. Appl. No. 14/357,335.
U.S. Appl. No. 14/357,335, filed May 9, 2014 in the name of Gueniche et al.
Ramadan, M.F. et al. "Oil Composition of Coriander (Coriandrum Sativum L.) Fruit-Seeds". European Food Research and Technology, vol. 215, pp. 204-209, 2002.
Mintel. "Cold Pressed Flaxseed Oil". GNPD, XP002678759, May 2010.
Mintel. "Essential Seed Omega Shake". GNPD, XP002678760, Oct. 2009.
Mintel. "Organic Omega Seed Oil". GNPD, XP002678761, Nov. 2005.
Mintel. "Energizing Drink Mix". GNPD, XP002678762, Aug. 2005.
Mintel. "*Lactobacillus* Supplement". GNPD, XP002678763, Mar. 2008.
Mar. 31, 2014 Search Report issued in International Patent Application No. PCT/IB2012/056262.
Mar. 31, 2014 Written Opinion issued in International Patent Application No. PCT/IB2012/056262.
Nov. 9, 2011 Written Opinion issued in French Patent Application No. 1160199.
Menon, K.N. et al. "Petroselinic Acid: Occurrence in Some Umbelliferae Seed Fats". Proceedings of the Indian Academy of Sciences, Section A, vol. 38, No. 2, pp. 128-131, 1953.
Spangenberg, J.E. et al. "Authentication of Vegetable Oils by Bulk and Molecular Carbon Isotope Analyses With Emphasis on Olive Oil and Pumpkin Seed Oil". Journal of Agricultural and Food Chemistry, vol. 49, pp. 1534-1540, 2001.
Lawry, M. "Biological Therapy and Nail Psoriasis". Dermatologic Therapy vol. 20, pp. 60-67, 2007.
Bernard, "La Vie Révélée Du Follicule De Cheveu Humain". Médecine Sciences, vol. 22, No. 2, pp. 138-143, 2006.
Mar. 29, 2012 Office Action issued in U.S. Appl. No. 12/518,959.
Jan. 25, 2013 Office Action issued in U.S. Appl. No. 12/518,959.
Jul. 31, 2014 Office Action issued in U.S. Appl. No. 12/518,959.
Feb. 16, 2016 Office Action issued in U.S. Appl. No. 12/518,959.
Mar. 12, 2015 Office Action issued in U.S. Appl. No. 12/518,959.
Monnier et al., "Nonenzymatic Glycosylation and Browning of Proteins in Vivo". American chemical Society, pp. 431-449, 1983.
Jaworksy et al., "Characterization of Inflammatory Infiltrates in Male Pattern Alopecia: Implications for Pathogenesis". British Journal of Dermatology, vol. 127, pp. 239-246, 1992.
Sueki et al., "Quantitative and Ultrastructural Analysis of Inflammatory Infiltrates in Male Pattern Alopecia". Acta Derm Venereol, vol. 79, pp. 347-350, 1999.
Tsevegsuren et al., "Geranium Sanguineum (Geraniaceae) Seed Oil: A New Source of Petroselinic and Vernolic Acid". Lipids, vol. 39, No. 6, pp. 571-576, 2004.
U.S. Appl. No. 12/518,959, filed Sep. 24, 2009 in the name of Gueniche et al.
Oct. 17, 2016 Office Action issued in U.S. Appl. No. 14/889,984.
Oct. 20, 2016 Office Action issued in U.S. Appl. No. 14/889,895.
Nov. 1, 2016 Office Action issued in U.S. Appl. No. 12/518,959.
Jan. 30, 2017 Office Action issued in U.S. Appl. No. 14/890,064.

(56) References Cited

OTHER PUBLICATIONS

Burdock, George A. et al. "Safety Assessment of Coriander (Coriandrum sativum L.) Essential Oil as a Food Ingredient". Food and Chemical Toxicology, 2009, vol. 47, pp. 22-34.
Story, Erica N. et al. "An Update on the Health Effects of Tomato Lycopene." Annual Review of Food Science and Technology, 2010, vol. 1, pp. 189-210.
Feb. 27, 2017 Office Action issued in Chinese Patent Application No. 201480038812.3.
Nan, Jinming et al. "Yu County SPA Recuperation Guidelines." Shanxi People's Publishing House, Edition 1, 1994, pp. 65-66.
Cheng, Hong-Yan et al. "Genetic Modifications on Industrial Characteristics of Seed Oils." Acta Botanica Yunnanica, vol. 30, No. 1, 2008, pp. 89-94.
Appendix.
Mar. 22, 2017 Office Action issued in U.S. Appl. No. 14/357,335.
Van De Kerkhof, Peter C.M. et al. "Brittle Nail Syndrome: A Pathogenesis-Based Approach with a Proposed Grading System." Journal of American Academy of Dermatology, 2005, vol. 53, No. 4, pp. 644-651.
Kitahara, Takashi et al. "Coexpression of Keratins Characteristic of Skin and Hair Differentiation in Nail Cells." Journal of Invetigative Dermatology, 1993, vol. 100, No. 2, pp. 171-175, specif. p. 171.
Apr. 20, 2017 Office Action Issued in U.S. Appl. No. 14/890,069.

\* cited by examiner

COMBINATION OF ACTIVE AGENTS FOR ORAL ADMINISTRATION FOR IMPROVING THE QUALITY OF NAILS

The present invention relates to the field of cosmetic products, for oral administration, intended for nailcare.

In particular, the present invention is directed toward proposing combinations of active agents that are useful for improving the quality of the nails, for reducing and/or avoiding the esthetic defects thereof, and/or for improving the general esthetic appearance of the nails.

More particularly, the present invention is directed toward proposing combinations of active agents that are capable of improving the microvascularization of the nails.

As will emerge hereinbelow, it is more particularly a matter in the context of the present invention of improving the quality of the nails and of their general esthetic appearance, especially in the case of pre-hypertensive individuals.

A nail or ungual plaque is a translucent, smooth, flexible horny blade which forms a surface excrescence of the skin, consisting of keratinocytes and a very dense and homogeneous keratin matrix. This matrix keeps the cells welded together and gives the nail its strength, hardness, solidity and flexibility. The nail is enveloped by an epidermal sheath, or matrix.

From a morphological viewpoint, a nail consists of a dorsal part, an intermediate part, a ventral part, a proximal matrix, an intermediate matrix, a lunula and the nail bed. 80% of the thickness of a nail is produced by the proximal matrix, and 20% of its thickness is produced by the intermediate matrix and the nail bed. The dorsal part consists of hard keratin, the intermediate part is the thickest and is formed of moderately hard keratin, and the ventral part consists of soft keratin.

The microvascular network of the nails is particularly dense and specialized. The nail lies on a microvascular network in loops, which are more or less stretched depending on the anatomical localization of the nail, and thus constitutes a favored region of exchange for supplying the nails with nutrients via the blood network.

As regards its chemical constitution, a nail contains water, lipids, mucopolysaccharides and minerals, such as sodium, potassium, iron, calcium, zinc or silicon, and keratin proteins.

The general quality of the nails, and also their general esthetic appearance, depend especially on their chemical constitution, in particular on their content of water, lipids and phospholipids. The supply of nutrients to the nails is also an important factor in the modification of their quality.

The inventors have recently demonstrated that there is a significant statistical link between the pre-hypertensive population and the quality of the nails. Specifically, it has been observed that the pre-hypertensive state significantly predisposes toward a poorer nail quality, and especially to premature breaking and delamination thereof.

Pre-hypertensive individuals in fact show a decrease in the functionality of the microvascular network of the nails. Thus, the nails of these individuals, which are less vascularized and thus less irrigated and consequently less nourished, are affected in their quality and in their general esthetic appearance.

Pre-hypertension is defined as being the top part of the range of normality of arterial hypertension, an individual lying within this range nonetheless being qualified as normotensive. Thus, a pre-hypertensive individual is not unwell. Such a case consequently lies outside the pathological field that may be represented, for example, by hypertension.

A pre-hypertensive individual is defined as having a systolic blood pressure ranging from 120 to 139 mmHg or a diastolic blood pressure ranging from 80 to 89 mmHg.

At the present time, the main solutions proposed in the field of nail quality are based on the use of nail varnishes, moisturizing active agents in handcare products, or chemical reinforcement of the nail. The latter solution is based on the use of nail-hardening agents, such as formaldehyde at 1-2%, which generate crossbonds in the keratin. However, frequent use of these products may give rise to too many crossbonds, paradoxically promoting embrittlement of the nails.

Temporary implants, such as false nails, have also been proposed in the field of nail quality, but their main objective is to hide the poor quality of the nails rather than to prevent it and/or to restore their quality. From a cosmetic viewpoint, there is thus a need to be able to reduce or prevent the various esthetic modifications that may affect the nails, especially in the case of pre-hypertensive individuals, and thus to improve the quality of the nails and their general esthetic appearance, and thus the esthetic appearance of the fingers, the hands and/or the feet.

Metalloprotein 9 (MMP-9) is an inducible ubiquitous protease that is capable of degrading collagen and elastin, and whose role in the impairment of vascular elasticity in relation with pre-hypertension has been demonstrated (Yasmin Sharon Wallace et al. Arterioscler. Thromb. Vasc. Biol. 2005). A direct link between an increase in the circulating levels of MMP-9 and pre-hypertension has thus been established. Specifically, MMP-9 is an important contributor to the establishment of a loss of elasticity of the vascular walls, to abnormal distension of the blood vessels and consequently to the development or maintenance of a pre-hypertensive state.

This protease thus intervenes in the impairment of the microvascularity of the nails in the case of pre-hypertensive individuals.

It thus emerges that MMP-9 would be a potential target for acting effectively on the integrity and quality of the microvascular network of the nails.

The characterization of active agents, or even of a combination of active agents, that are capable of inhibiting the activity of MMP-9 would thus make it possible to reinforce or to restore the microvascular network of the nails, especially in the case of pre-hypertensive individuals, thus making it possible to improve or maintain the quality of the nails and their general esthetic appearance.

The present invention is specifically directed toward meeting this need.

The inventors have thus discovered that a combination comprising at least petroselinic acid and an additional component chosen from taurine, arginine, cysteine, zinc, and a salt thereof, lycopene and zinc, in particular Zn(II) salts, preferably complexed with one or more (poly)hydroxy acids, such as zinc gluconate, proves, surprisingly, to be active for inhibiting MMP-9.

The efficacy of this combination is all the more surprising since petroselinic acid, used in isolated form, shows no inhibitory activity toward MMP-9, as emerges from the experimental section below.

On the other hand, petroselinic acid is already known for its efficacy in various applications, such as the moisturization of dry skin in EP 0 709 084 or the treatment of dandruff and itchy scalp in EP 0 116 439.

As illustrated in the examples of the present document, the inventors have in point of fact noted that a combination of active agents in accordance with the invention proves to be capable of synergistically inhibiting the basal level of synthesis and/or release of MMP-9 by keratinocytes.

More precisely, a combination of active agents according to the invention makes it possible efficiently to improve the microvascularity of the nails, to improve the quality of the nails, and also their general esthetic appearance, and similarly the general esthetic appearance of the fingers, the hands and/or the feet.

The present invention in particular proposes a combination of petroselinic acid with at least one active agent chosen from taurine, arginine, cysteine, and a salt thereof, lycopene and zinc, or a salt thereof, in particular a Zn(II) salt, preferably complexed with one or more (poly)hydroxy acids, such as zinc gluconate, intended for oral administration.

A main subject of the invention is thus the oral cosmetic use of a combination of active agents comprising at least petroselinic acid and at least one active agent chosen from taurine, arginine, cysteine, zinc, a salt thereof, and lycopene, for improving the quality of the nails, preferably in the case of a pre-hypertensive individual.

The present invention also relates to the oral cosmetic use of a combination of active agents according to the invention, for improving the microvascularization of the nails.

The present invention also relates to the oral cosmetic use of a combination of active agents according to the invention, for improving the general esthetic appearance of the nails.

The present invention also relates to the oral cosmetic use of a combination of active agents according to the invention, for improving the general esthetic appearance of the fingers, the hands and/or the feet.

The invention is also directed toward the use of a combination of active agents according to the invention, used in a cosmetic composition for oral administration or in a food supplement.

A cosmetic composition for oral administration or a food supplement according to the invention offers the same advantages as those afforded by the combination in accordance with the invention, as indicated previously.

The uses according to the invention are preferably intended for a pre-hypertensive individual.

The invention also relates to a cosmetic process for improving the quality of the nails and/or the general esthetic appearance of the nails, in the case of an individual in need thereof, especially in the case of a pre-hypertensive individual, comprising the oral administration to said individual of a combination of active agents, of a composition or of a food supplement in accordance with the invention.

A combination of active agents, a composition or a food supplement according to the invention may be used daily for several months, without a medical prescription. The present invention thus clearly lies outside the therapeutic field.

The present invention is also directed toward a kit or packaging assembly comprising:
(i) a combination of active agents, or a food supplement, in accordance with the invention, and
(ii) an antifungal agent intended for topical application, the combination, or the supplement (i), and the antifungal agent (ii) being intended to be administered independently of each other, separately, simultaneously or sequentially over time, the antifungal agent (ii) preferably being administered before the combination, or the supplement (i).

The present invention is also directed toward a kit or packaging assembly comprising:
(i) a combination of active agents, or a food supplement, in accordance with the invention, and
(ii) a moisturizer and/or a hardener intended for topical application,
the combination, or the supplement (i), and the moisturizer and/or hardener (ii) being intended to be administered independently of each other, separately, simultaneously or sequentially over time.

According to one embodiment, a kit according to the invention uses an antifungal agent. Such an agent may be chosen from the imidazole, morpholine or pyridone families.

According to another embodiment, a kit according to the invention uses a moisturizer and/or a hardener.

A moisturizer in accordance with the invention may be chosen from vitamins and oils. As examples of oils that are suitable for use as moisturizers, mention may be made especially of argan oil, sesame seed oil and sunflower oil.

A hardener in accordance with the invention may be chosen from hydrolyzed wheat protein, calcium pantothenate or vitamin B5, iron, epoxy resins and polyesters, and nitrocellulose.

The term "improving the quality of the nails" means improving their hardness, and/or their solidity, and/or their resistance to impacts and/or to external attacking factors, and/or their resistance to splitting, and/or their smooth appearance, and/or their sheen, and/or their rate of regeneration and/or of growth, and/or their color homogeneity, and/or their transparency and/or their flexibility.

Pre-hypertensive individuals are particularly concerned as regards the uses and processes according to the invention.

The invention also relates to a food supplement comprising one part of the compounds forming the combination of active agents in accordance with the invention in a first composition, and at least the other part of the compounds forming the combination of active agents in a second composition, as a kit or combination product for simultaneous use, separate use or sequential use over time.

It is understood in the context of the present invention that "the oral cosmetic use" covers the use of products administered orally, these products being, for example, in the form of a food supplement as outlined below. These products produce an esthetic effect on the nails, or alternatively an effect which has a beauty purpose, for example with a view to protecting them, keeping them in good condition, and in particular making them more attractive.

Combination of Active Agents
1. Petroselinic Acid

The term "petroselinic acid-rich oil" means an oil comprising at least 20% of petroselinic acid and more preferentially more than 30% of petroselinic acid.

Alternatively, petroselinic acid, or monounsaturated fatty acid (C18:1 n-12 or cis delta 6) or C18 delta-6-cis-octadecenoic acid, is used in a combination of active agents in accordance with the invention.

Umbellifera plants are plants whose flowers are arranged in umbels. Species that are particularly rich in petroselinic acid are Umbellifarea-Apiacea and Araliaceae. Plants of the *Thapsia* genus are also sources of petroselinic acid (Avato et al., Lipids, 2001, 36, 845). The species preferably used in the invention are coriander, chervil, carrot, celery, cumin, caraway, parsley and dill. The umbellifera plant oil used according to the invention may be extracted from the seeds of these umbellifera plants, for example by grinding or pressing, followed by refining. The umbellifera plant oil has a petroselinic acid content which varies according to the umbellifera plant seed from which it is extracted. For the same umbellifera plant, the petroselinic acid content also varies according to the country of origin of the umbellifera plant and according to the extraction, which may be more or less complete.

Petroselinic acid is also an abundant compound (approximately 48%) of *Geranium sanguineum* seed oil, and also of *Coriandrum sativum* coriander seed oil (about 65%).

According to one embodiment, petroselinic acid is used in the present invention in an isolated form or in the form of a plant extract containing same, in particular in the form of an oil.

Thus, according to one embodiment, the use that is the subject of the present invention is such that petroselinic acid is used in the form of umbellifera plant oil or *Geranium sanguineum* oil, preferably in the form of a coriander (*Coriandrum sativum*) oil.

The umbellifera plant oil is preferably chosen from a dill, parsley, caraway, cumin, celery, carrot, chervil or coriander seed oil, or mixtures thereof, the umbellifera plant oil preferably being a coriander (*Coriandrum sativum*) seed oil.

The contents are variable depending on whether the combination of active agents in accordance with the invention is used in a cosmetic composition intended for oral administration or in the form of a food supplement.

The petroselinic acid content, in a cosmetic composition intended for oral administration or in a food supplement in accordance with the invention, may be between 10% and 70% by weight, especially between 15% and 70% by weight, and particularly between 20% and 70% by weight, relative to the total weight of said combination of active agents.

The petroselinic acid content in a cosmetic composition intended for oral administration or in a food supplement in accordance with the invention may be such that the daily dose of said petroselinic acid is between 5 and 1000 mg/day and especially between 50 and 650 mg/day.

2. Taurine, Arginine, Cysteine, Zinc and Lycopene

A combination of active agents according to the invention also comprises at least one active agent chosen from taurine, or hypotaurine, arginine, cysteine, zinc and lycopene.

It may also use at least one of the salts of taurine or of hypotaurine, of arginine, of cysteine or of zinc. Insofar as the combination according to the invention is intended for oral use in an individual, the salts that may be used are obviously chosen for their total harmlessness. Alkali metal or alkaline-earth metal salts, in particular magnesium salts, manganese, iron(II) or zinc salts are suitable in this respect.

As regards zinc, Zn(II) salts and preferably those complexed with one or more (poly)hydroxy acids are especially suitable for the purposes of the invention.

According to one embodiment, a zinc salt used in a combination, a composition or a food supplement in accordance with the invention is zinc gluconate.

The total content of taurine, hypotaurine, arginine and/or cysteine, or a salt thereof, in a cosmetic composition intended for oral administration or in a food supplement in accordance with the invention, may be between 5% and 90% by weight, especially between 5% and 50% by weight, and particularly between 5% and 40% by weight, relative to the total weight of said combination of active agents.

The total content of taurine, hypotaurine, arginine and/or cysteine, or a salt thereof, in a cosmetic composition intended for oral administration or in a food supplement in accordance with the invention may be such that the daily dose of said taurine, arginine and/or cysteine is between 10 and 700 mg/day and especially between 50 and 250 mg/day.

The content of zinc, or a salt thereof, in particular of zinc gluconate, in a cosmetic composition intended for oral administration or in a food supplement in accordance with the invention may be between 0.001% and 40% by weight, especially between 0.01% and 40% by weight and particularly between 0.1% and 20% by weight relative to the total weight of the combination of active agents.

The content of zinc, or a salt thereof, especially of zinc gluconate, in a cosmetic composition intended for oral administration or in a food supplement in accordance with the invention may be such that the daily dose of said zinc or a salt thereof is between 0.01 and 300 mg/day, especially between 0.1 and 200 mg/day, and in particular between 1 and 100 mg/day.

Lycopene is a natural pigment found in ripe fruit, particularly in tomato, or synthesized, especially from a fungus, *Blakeslea trispora*. It belongs to the carotenoid family and its structure is similar to that of β-carotene.

It may in particular be sold by the company Lycored under the name Lyc-O-Mato®.

Preferably, the combination of active agents in accordance with the invention comprises, besides petroselinic acid, at least lycopene.

The lycopene content, in a cosmetic composition intended for oral administration or in a food supplement in accordance with the invention, may be between 0.1% and 30% by weight, especially between 0.1% and 20% by weight, and particularly between 0.1% and 10% by weight, relative to the total weight of the combination of active agents.

The lycopene content in a cosmetic composition intended for oral administration or in a food supplement in accordance with the invention may be such that the daily dose of said lycopene is between 0.1 and 20 mg/day and especially between 0.5 and 10 mg/day.

Preferably, taurine, or at least one salt thereof, is used in a combination of active agents in accordance with the invention. In other words, the combination of active agents according to the invention preferably comprises, or even consists of at least petroselinic acid and taurine.

Preferably, lycopene is used in a combination of active agents in accordance with the invention. In other words, the combination of active agents according to the invention preferably comprises at least petroselinic acid and lycopene.

Preferably, arginine is used in a combination of active agents in accordance with the invention. In other words, the combination of active agents according to the invention preferably comprises at least petroselinic acid and arginine.

Preferably, zinc or a salt thereof is used in a combination of active agents in accordance with the invention. In other words, the combination of active agents according to the invention preferably comprises at least petroselinic acid and zinc or a salt thereof, preferably zinc gluconate.

Preferably, cysteine is used in a combination of active agents in accordance with the invention. In other words, the combination of active agents according to the invention preferably comprises at least petroselinic acid and cysteine.

A composition or a food supplement according to the invention may also comprise at least one agent chosen from a milk hydrolyzate tripeptide Val-Pro-Pro and/or Ile-Pro-Pro, an aqueous concentrate of tomato, a flavonoid, CoQ10, acetyl carnitine, alpha-lipoic acid and citrulline.

According to one embodiment, a composition or a food supplement according to the invention comprises zinc or a salt thereof.

As indicated previously, the zinc salt that is preferred according to the invention is zinc gluconate.

Thus, according to a preferred embodiment of the invention, a composition or a food supplement according to the invention comprises petroselinic acid, taurine and zinc, in particular zinc gluconate.

According to one embodiment, a cosmetic composition intended for oral administration or a food supplement in accordance with the invention comprises:

(i) petroselinic acid in a content of between 10% and 70% by weight, especially between 15% and 70% by weight and particularly between 20% and 70% by weight relative to the total weight of the combination of active agents;

(ii) taurine in a content of between 5% and 90% by weight, especially between 5% and 50% by weight and particularly between 5% and 40% by weight relative to the total weight of the combination of active agents; and (iii) optionally zinc or a salt thereof, preferably a zinc (poly)hydroxy acid, preferentially zinc gluconate, in a content of between 0.001% and 40% by weight, especially between 0.01% and 40% by weight and particularly between 0.1% and 20% by weight relative to the total weight of the combination of active agents;

(iv) optionally vitamin D3 in a content of between 0.0001% and 1.0% by weight, especially between 0.0001% and 0.5% by weight and particularly between 0.0001% and 0.1% by weight relative to the total weight of the combination of active agents; and/or (v) optionally vitamin E or a derivative thereof, preferably tocopheryl acetate, in a content of between 0.01% and 10% by weight, especially between 0.1% and 10% by weight and particularly between 0.2% and 5% by weight relative to the total weight of the combination of active agents.

According to a particular embodiment, a cosmetic composition for oral administration or a food supplement in accordance with the invention comprises ingredients i) and ii) and optionally ingredient iii) indicated previously.

According to a particular embodiment, a cosmetic composition for oral administration or a food supplement in accordance with the invention comprises ingredients i) to v) below, taken together or individually:

(i) petroselinic acid in a content of between 1% and 70% by weight, especially between 10% and 70% by weight and particularly between 20% and 70% by weight relative to the total weight of the composition or of the supplement;

(ii) taurine in a content of between 5% and 90% by weight, especially between 5% and 50% by weight and particularly between 5% and 40% by weight relative to the total weight of the composition or of the supplement; and/or (iii) at least one zinc (poly)hydroxy acid, preferably zinc gluconate, in a content of between 0.001% and 40% by weight, especially between 0.01% and 40% by weight and particularly between 0.1% and 20% by weight relative to the total weight of the composition or of the supplement;

(iv) optionally vitamin D3 in a content of between 0.0001% and 1.0% by weight, especially between 0.0001% and 0.5% by weight and particularly between 0.0001% and 0.1% by weight relative to the total weight of the composition or of the supplement; and/or (v) optionally vitamin E or a derivative thereof, preferably tocopheryl acetate, in a content of between 0.01% and 10% by weight, especially between 0.1% and 10% by weight and particularly between 0.2% and 5% by weight relative to the total weight of the composition or of the supplement.

According to a particular embodiment, the cosmetic composition for oral administration or the food supplement in accordance with the invention comprises all of the above-mentioned ingredients (i) to (v).

Such a composition of food supplement or oral composition type in accordance with the invention may in particular have the following contents:

| Components | % by weight relative to the total weight of the composition |
| --- | --- |
| Petroselinic acid | 54.9 (provided by the coriander seed oil) |
| Zinc gluconate | 6.3 (of which 13.6% of active material) |
| Taurine | 18.7 (of which 98.5% of active material) |
| Vitamin E | 1.0 (of which 67% of active material) |
| Vitamin D3 | 0.03 (of which 2.5% of active material) |

For ingestion, numerous embodiments of oral compositions and especially of food supplements are possible. Their formulation is performed via the usual processes for producing coated tablets, gel capsules, gels, emulsions, tablets, lozenges or soft capsules.

According to the present invention, a cosmetic composition for oral administration or a food supplement in accordance with the invention may also comprise at least one vitamin chosen from vitamin B1, B3, B5, B6, B8, B12, C, D, and especially D3, and tocopherol (vitamin E) and derivatives thereof, especially an ester such as tocopheryl acetate or palmitate, preferably tocopheryl acetate.

According to one embodiment, a cosmetic composition for oral administration or a food supplement in accordance with the present invention preferably comprises at least vitamin E or a derivative thereof and/or vitamin D, preferentially vitamin D3 and/or tocopheryl acetate.

According to a particular embodiment, a cosmetic composition for oral administration or a food supplement in accordance with the present invention comprises vitamin D3 and tocopheryl acetate.

Thus, according to one embodiment, a cosmetic composition intended for oral administration or a food supplement in accordance with the invention comprises petroselinic acid, taurine, zinc or a salt thereof, preferably zinc gluconate, vitamin D3 and tocopheryl acetate.

The compositions or food supplements according to the invention may also comprise at least one active agent chosen from glucosamine, collagen and hyaluronic acid.

The compositions or food supplements according to the invention may also comprise at least one active agent chosen from an extract of rosemary, rosmarinic acid, carnosic acid, curcumin, extract of pine bark, pycnogenol, berberin, extract of *Boswellia*, emodin, sesamol, sulforaphane, extract of broccoli, resveratrol, extract of grape, 6-shogaol, extract of blackcurrant, extract of aubergine, enterolactone, extract of loquat, oleuropein, pachymic acid, pterostilbene, hydroxytyrosol, and omega-3 and omega-6 polyunsaturated fatty acids PUFA and monounsaturated fatty acids MUFA.

The oral compositions or the food supplements according to the invention may also comprise at least one probiotic, a prebiotic or a mixture of probiotics and a mixture of prebiotics. As probiotic microorganisms, mention may be made especially of *Lactobacillus johnsonii* or *Lactobacillus paracasei*.

The compositions according to the invention, intended for oral administration, may comprise all or only a part of the daily dose.

In other words, one to three compositions may be administered per day.

Typically, the duration of this cosmetic treatment for oral administration may be greater than 4 weeks, especially from 4 to 24 weeks, with, where appropriate, one or more periods of stoppage.

Other characteristics and advantages of the invention will emerge more clearly from the examples that follow, which are given as non-limiting illustrations.

EXAMPLE 1

Characterization of Embrittled/Split Nails Versus Normal Nails in Relation with a State of Pre-Hypertension Seventy healthy women, from 18 to 50 years old, were included in the study indicated in the rest of the present text. Of these 70 women, 35 had embrittled/split nails and 35 had normal nails.

The embrittled nature of the nails was confirmed by a clinical evaluation using the scale published previously by Van de Kerkhof (van de Kerkhof P C, Pasch M C, Scher R K, Kerscher M, Gieler U, Haneke E, Fleckman P. Brittle nail syndrome: a pathogenesis-based approach with a proposed grading system. *J. Am. Acad. Dermatol.* 2005 October; 53(4): 644-51.), which scale takes into account the onychoschizia (transverse and lamellar splitting) and the onychorrhexis (striations and longitudinal breaks) of the tested nails. These evaluations were performed on the most damaged nail chosen by the clinician on one of the two hands.

In the course of this study, a measurement of the arterial pressure was taken according to a method well known to those skilled in the art.

Entirely surprisingly, a statistically significant difference in systolic pressure was revealed in the case of the subjects having embrittled/split nails in comparison with the population having normal nails.

|  | Normal nails (n = 42) | Embrittled/split nails (n = 42) | Inter-group comparison (p-value) t-test |
|---|---|---|---|
| Systolic pressure (mmHg) | 114.929 ± 10.538 | 121.238 ± 10.529 | S, p = 0.007 |

The state of pre-hypertension corresponds in JNC VII to a systolic pressure of between 120-139 mmHg (*JNC VII Express. The seventh report of the joint national committee on prevention, detection, evaluation and treatment of high blood pressure. National Institute of Health; Washington D.C.* 2003; *Publication No.* 03-5233). The population of women with embrittled/split nails included in this study may thus be considered as a healthy population presenting with pre-hypertension.

EXAMPLE 2

Demonstration of the Inhibitory Effect of Combinations of Active Agents According to the Invention on the Basal Synthesis/Release of MMP-9 by Human Epidermal Keratinocytes Numerous cell types are capable of producing MMP-9: endothelial cells, immune cells, connective cells and keratinocytes.

Human skin keratinocytes were chosen as experimental model for in vitro evaluation on account of their high availability and of their ease of use, and also for their analogy with endothelial cells insofar as they contribute to the formation of epithelia.

Specifically, hair endothelial cells are harder to obtain. Similarly, their high sensitivity to proteases does not make it possible, in contrast with keratinocytes in culture, to test simply and reproducibly the effect of the modulators of these MMPs. This is especially due to inhibitory effects on the growth of these cells of the degradation products (angiostatins) produced by the majority of MMPs (Brauer et al. BMC Biochemistry 2011, 12: 38).

Moreover, in the nail, as in the hair, a close anatomical proximity exists between the keratinocytes and the blood vessels, suggesting that the keratinocytes may also be one of the sources of production of MMP-9 capable of altering the physiology of the blood vessels and of the nails.

Active agents in accordance with the invention in isolated or non-isolated form were tested on normal human epidermal keratinocytes (NHEK) so as to determine their effect on the basal level of synthesis and/or release of metalloprotease 9 (MMP-9) by these cells.

Table I below presents the nature of the compounds tested (alone or in combination—1st column) and the results obtained (2nd column).

This test was performed on cells cultured at 37° C., 5% $CO_2$. The culture medium is Keratinocyte-SFM supplemented with epidermal growth factor (EGF) at 0.25 ng/ml, pituitary extract (PE) at 25 µg/ml and gentamicin at 25 µg/ml.

The keratinocytes were cultured in the culture medium indicated above for 24 hours. The cells were then treated, or not (for the control), with the compounds or combinations of compounds indicated in Table I below, and incubated for 24 hours at the doses indicated in Table I.

At the end of this incubation, the culture supernatants were collected and stored so as to assay the amounts of MMP-9 secreted using the ELISA R&D Systems assay kit of reference DY911.

The inter-group comparisons were performed using the unpaired bilateral Student's t-test.

The variations in the amounts measured are indicated in Table I below.

TABLE I

| Compounds/combinations of compounds tested | % of basal synthesis/release of MMP-9 by keratinocytes |
|---|---|
| Petroselinic acid alone (0.1 µM) | −12% (ns) |
| Arginine alone (1.7 µg/ml) | −11% (ns) |
| Arginine (1.7 µg/ml) + petroselinic acid (0.1 µM) | −33%* |
| Taurine alone (1.2 µg/ml) | +11% (ns) |
| Taurine (1.2 µg/ml) + petroselinic acid (0.1 µM) | −27%* |
| Cysteine alone (1.2 µg/ml) | −12% (ns) |
| Cysteine (1.2 µg/ml) + petroselinic acid (0.1 µM) | −30%* |
| Lyc-o-mato alone ($10^{-5}$%) | +26% (ns) |
| Lycomato ($10^{-5}$%) + petroselinic acid (0.1 µM) | −24%* |

(ns): not significant relative to the basal level of synthesis and/or of release of MMP-9.
*significant relative to the basal level of synthesis and/or of release of MMP-9.

First, it may be noted that none of the compounds tested, when they are used individually, significantly inhibits the basal level of synthesis and/or release of MMP-9. Certain compounds (lycomato and taurine) even show a reverse and moderate tendency, without this, however, being significant.

In contrast, the combinations of active agents in accordance with the invention do indeed show significant inhibition of the basal level of synthesis and/or release of MMP-9.

Specifically, a decrease in the amount of MMP-9 in the culture medium of the treated keratinocytes may be observed relative to the amount present in the absence of treatment, or even in the presence of each of the elements tested taken individually. This consequently indicates a decrease in the basal level of synthesis and/or the release of MMP-9 by these cells in the presence of a combination of active agents according to the invention.

It is thus indeed a synergistic effect of the combinations in accordance with the invention that is observed and demonstrated here. Specifically, active agents with no effect individually on the synthesis and/or release of MMP-9 by the keratinocytes do, however, show such an effect when they are combined in accordance with the present invention.

EXAMPLE 3

Oral Composition in Soft Capsule Form

| | (mg/soft capsule) |
|---|---|
| Ingredients | |
| Coriander seed oil (65% petroselinic acid) | 300 |
| Taurine | 76.10 |
| Zinc gluconate | 25.75 |
| Vitamin E | 4.10 |
| Vitamin D3 | 0.115 |
| Excipients | |
| Refined coconut oil | 112 |
| Yellow beeswax, Cera flava | 22 |
| Sunflower lecithin | 10 |
| Capsule | |
| Fish gelatin | 144.6 |
| Glycerol | 58.6 |
| Purified water | 6.8 |

When this composition is administered orally to an individual, at a rate of two wafer capsules per day, an improvement in the quality and the general esthetic appearance of the nails may be observed in this individual.

These effects are even more visible when the individual tested is pre-hypertensive, insofar as his nails are, before the test, of poor quality and have a mediocre or even poor general esthetic appearance.

A combination of active agents in accordance with the invention allows a better supply of nutrients via the blood to the cells perfused with these microvessels, thus protected against attack associated with the activity of MMP-9, and consequently a better quality and a better general esthetic appearance of the nail and of the surrounding skin.

EXAMPLE 4

Oral Composition as a Stick in Emulsion Form

| | (g/stick) |
|---|---|
| Ingredients | |
| Coriander seed oil (of which 65% of petroselinic acid) | 0.65 |

| | (g/stick) |
|---|---|
| Taurine | 0.0515 |
| Vitamin E | 0.0082 |
| Lycopene | 0.005 |
| Excipients | |
| Water | 1.722 |
| Sugar | 0.911 |
| Fructose | 0.911 |
| Microcrystalline cellulose | 0.032 |
| Sodium carboxymethylcellulose | 0.004 |
| Natural mixture of tocopherols | 0.034 |
| Sunflower oil | 3.015 |
| Natural lemon flavoring | 0.034 |
| Potassium sorbate | 0.013 |
| Citric acid | 0.013 |
| Propylene glycol alginate | 0.010 |

EXAMPLE 5

Oral Composition in Soft Capsule Form

| | (mg/soft capsule) |
|---|---|
| Ingredients | |
| Coriander seed oil (65% petroselinic acid) | 300 |
| Arginine | 82 |
| Cysteine | 25 |
| Vitamin E | 4.10 |
| Excipients | |
| Refined coconut oil | 112 |
| Yellow beeswax, Cera flava | 22 |
| Sunflower lecithin | 10 |
| Capsule | |
| Fish gelatin | 144.6 |
| Glycerol | 58.6 |
| Purified water | 6.8 |

The invention claimed is:

1. A cosmetic method for improving the hardness, and/or the solidity, and/or the resistance to impacts and/or to external attacking factors, and/or the resistance to splitting, and/or the smooth appearance, and/or the sheen and/or the rate of regeneration and/or of growth, and/or the color homogeneity, and/or the transparency, and/or the flexibility of the nails comprising at least a step consisting of an oral administration of a combination of active agents comprising at least petroselinic acid and at least one active agent chosen from taurine, arginine, cysteine, zinc, a salt thereof, and lycopene.

2. The method according to claim 1, wherein said petroselinic acid is used in an isolated form or in the form of a plant extract containing same.

3. The method according to claim 1, wherein said petroselinic acid is in the form of an oil.

4. The method as claimed in claim 1, wherein said petroselinic acid is used in the form of an umbellifera plant oil or *Geranium sanguineum* oil.

5. The method as claimed in claim 4, in which said umbellifera plant oil is chosen from dill, parsley, caraway, cumin, celery, carrot, chervil and coriander seed oils, and mixtures thereof.

6. The method as claimed in claim 1, in which the combination of active agents comprises at least petroselinic acid and taurine.

7. The method as claimed in claim 1, in which the combination of active agents comprises at least petroselinic acid and lycopene.

8. The method as claimed in claim 1, in which the combination of active agents comprises at least petroselinic acid and arginine.

9. The method as claimed in claim 1, in which the combination of active agents comprises at least petroselinic acid and zinc, optionally in the form of a Zn(II) salt.

10. The method as claimed in claim 1, in which the combination of active agents comprises at least petroselinic acid and cysteine.

11. The method as claimed in claim 1, in which the combination of active agents is used in a food supplement.

12. The method as claimed in claim 11, in which the food supplement also comprises at least one agent chosen from a milk hydrolyzate tripeptide Val-Pro-Pro and/or Ile-Pro-Pro, an aqueous concentrate of tomato, a flavonoid, CoQ10, acetyl carnitine, alpha-lipoic acid and citrulline.

13. The method as claimed in claim 11, in which said food supplement comprises:
   (i) petroselinic acid, in isolated form or in the form of an umbellifera plant oil, in a content of between 10% and 70% by weight, relative to the total weight of the combination of active agents;
   (ii) taurine, or a salt thereof, in a content of between 5% and 90% by weight, relative to the total weight of the combination of active agents; and
   (iii) optionally zinc, or a salt thereof, in a content of between 0.001% and 40% by weight, relative to the total weight of the combination of active agents.

14. The method as claimed in claim 11, in which the food supplement also comprises at least one vitamin chosen from vitamin B1, B3, B5, B6, B8, B9, B12, C, D, or vitamin E and derivatives thereof.

15. The method as claimed in claim 14, in which the food supplement comprises petroselinic acid, taurine, zinc gluconate, vitamin D3 and tocopheryl acetate.

16. A food supplement comprising one part of the compounds forming the combination of active agents as defined in claim 1 in a first composition, and at least the other part of the compounds forming said combination of active agents in a second composition, as a kit or combination product for simultaneous use, separate use or sequential use over time.

17. A kit comprising:
   (i) a combination of active agents as defined in claim 1, optionally under the form of a food supplement, and
   (ii) an antifungal agent intended for topical application, the combination, or the supplement (i), and the antifungal agent (ii) being intended to be administered independently of each other, separately, simultaneously or sequentially over time, the antifungal agent (ii) being optionally administered before the combination, or the supplement (i).

18. A kit comprising:
   (i) a combination of active agents as defined in claim 1, optionally in the form of a food supplement, and
   (ii) a moisturizer and/or a hardener intended for topical application,
the combination or the supplement (i) and the moisturizer and/or hardener (ii) being intended to be administered independently of each other, separately, simultaneously or sequentially over time.

* * * * *